(12) United States Patent
Uyama

(10) Patent No.: US 6,653,272 B1
(45) Date of Patent: Nov. 25, 2003

(54) DETERGENT COMPOSITION

(76) Inventor: Shizuo Uyama, 19-12, Shinonome 1-chome, Minami-ku, Hiroshima-shi, Hiroshima 734-0022 (JP)

(*) Notice: Subject to any disclaimer, the term of this patent is extended or adjusted under 35 U.S.C. 154(b) by 0 days.

(21) Appl. No.: 09/926,456

(22) PCT Filed: May 11, 2000

(86) PCT No.: PCT/JP00/03004

§ 371 (c)(1), (2), (4) Date: Nov. 7, 2001

(87) PCT Pub. No.: WO00/70007

PCT Pub. Date: Nov. 23, 2000

(30) Foreign Application Priority Data

May 12, 1999 (JP) .............................. 11/131120

(51) Int. Cl.⁷ .............................. C12S 9/00; C11D 7/42; C12N 9/98; C07D 211/54
(52) U.S. Cl. ................. 510/392; 510/392; 510/393; 510/630; 510/236; 435/187; 546/243
(58) Field of Search ................. 510/392, 393, 510/530, 236; 435/187; 546/243

(56) References Cited

U.S. PATENT DOCUMENTS

| | | | | |
|---|---|---|---|---|
| 4,063,017 A | | 12/1977 | Tsao et al. | |
| 4,335,002 A | * | 6/1982 | Mussinan et al. | 252/1 |
| 4,351,849 A | * | 9/1982 | Meade | 426/61 |
| 4,822,886 A | * | 4/1989 | Donovan | 546/243 |
| 5,464,766 A | * | 11/1995 | Bruno | 210/601 |
| 5,629,278 A | * | 5/1997 | Baeck et al. | 510/236 |
| 6,074,631 A | * | 6/2000 | Tsuchiya et al. | 424/65 |

FOREIGN PATENT DOCUMENTS

| | | |
|---|---|---|
| JP | 8-157352 | 6/1996 |
| JP | 11-43428 | 2/1999 |

* cited by examiner

Primary Examiner—John Hardee
Assistant Examiner—Preeti Kumar
(74) Attorney, Agent, or Firm—Armstrong, Westerman, & Hattori, LLP

(57) ABSTRACT

A detergent composition that contains inorganic powder and a soap such as a soda soap, wherein the inorganic powder is zeolite powder, calcium carbonate powder, silica powder, ceramic powder, alga fossil powder, seashell powder or the like, and pineapple enzymes are fixed thereto by adding pineapple juice thereto and fermenting. This detergent composition does not cause water pollution like synthetic detergents do, thus enabling water pollution caused by wastewater from cleaning to be prevented. Moreover, due to the positive water-cleaning action of the pineapple enzymes, the detergent composition cleans the insides of drainage pipes, purifier tanks and the like, thus improving the functions thereof. Water pollution can thus be ameliorated.

5 Claims, No Drawings

DETERGENT COMPOSITION

TECHNICAL FIELD

The present invention relates to a detergent composition, and more particularly to a detergent composition that can be used, for example, in cleaning tableware, cooking appliances, sinks and the like in household kitchens, and cleaning tableware, food processing appliances, kitchen equipment and the like at food processing sites.

BACKGROUND ART

Water pollution greatly affects human health. Sources of water pollution include domestic wastewater, industrial wastewater and agricultural wastewater, and things that cause water pollution include microorganisms, chemical substances, industrial and other waste, and foreign matter in sewage water. Of these things that cause water pollution, petroleum-based synthetic detergents used for cleaning tableware, cooking appliances, sinks and the like in households and at food processing sites and the like have good cleaning power, but unlike soaps, are not readily biodegraded into harmless substances by microorganisms, and thus persist in water. Moreover, unlike industrial wastewater that is generated from localized sources, wastewater from cleaning that contains such synthetic detergents is discharged from the kitchens and the like of all households, and hence the source of this wastewater extends over a broad range, and thus even though such wastewater from cleaning is a large cause of water pollution, treating this wastewater efficiently is extremely difficult. In recent years, with a view to reducing the use of synthetic detergents that cause water pollution, soaps have thus been looked at anew. However, soaps are inescapably inferior to synthetic detergents in terms of cleaning power, and hence the current situation is that soaps are only used a very little compared with synthetic detergents, and thus water pollution caused by synthetic detergents is not really improving but rather continues to worsen.

In view of the current water pollution situation as described A above, an object of the present invention is thus to provide a detergent composition that does not cause water pollution like synthetic detergents do, thus enabling water pollution caused by wastewater from cleaning to be prevented, and moreover has a positive water-cleaning action, thus cleaning the insides of drainage pipes, purifier tanks and the like and improving the functions thereof, and enabling water pollution to be ameliorated.

DISCLOSURE OF THE INVENTION

The present inventors carried out assiduous studies to attain the above object. The present inventors came up with the idea that if a soap is used as a surfactant in a detergent composition instead of a synthetic detergent that causes water pollution, and moreover the detergent composition is made to contain a substance that has a water-cleaning action, then it should be possible to clean wastewater and ameliorate water pollution without requiring any special treatment equipment or any special effort. The present inventors then discovered that pineapple enzymes extracted from pineapple juice and having a plurality of types of enzyme action of decomposing macromolecular compounds are effective as such a substance having a water-cleaning action, thus arriving at the present invention.

The detergent composition of the present invention is thus characterized by containing a soap and an inorganic powder to which pineapple enzymes have been fixed. It is preferable to fix the pineapple enzymes to the inorganic powder by adding pineapple juice to the inorganic powder and then fermenting. Moreover, a zeolite powder, a calcium carbonate powder, a silica powder, a ceramic powder, an alga fossil powder, a seashell powder or the like can be used as the inorganic powder, and furthermore the inorganic powder is preferably porous.

According to the detergent composition of the present invention, synthetic detergents that cause water pollution are not used, but rather a soap that is biodegraded by microorganisms into harmless substances is used, and hence the detergent composition will not cause water pollution. Moreover, every time cleaning is carried out using the detergent composition, the pineapple enzymes having a water-cleaning action and an unpleasant-odor-eliminating action are discharged with the wastewater from the cleaning from drainage pipes into a purifier tank, sewage water or the like, and hence the aqueous environment can be improved. Furthermore, the detergent composition exhibits excellent cleaning effects due to synergy between the cleaning action of the soap and the abrasive action of the inorganic powder to which the pineapple enzymes have been fixed, and moreover the luster of metal (for example stainless steel) tableware, sinks and the like is restored, the insides of drainage pipes are cleaned, and unpleasant odors are eliminated.

The above-mentioned pineapple enzymes include a plurality of types of enzyme that carry out decomposition such as dehydrogenation, decarboxylation, deamination, desulfurization and dechlorination, and thus exhibit a plurality of enzymatic decomposition functions on various pollution-causing substances in wastewater. The BOD and COD of the wastewater, the amount of suspended solids (SS) in the wastewater, and the like are thus reduced. Moreover, organic chlorine compounds and some inorganic chlorine compounds contained in wastewater and sewage water are decomposed by the pineapple enzymes into harmless small molecules. Furthermore, the pineapple enzymes saccharify organic matter in wastewater with glucose, and decompose nitrogen compounds (such as nitrates) into amino acids, thus promoting the cleaning of the wastewater. Moreover, the pineapple enzymes introduce a large amount of oxygen into the wastewater during the process of decomposition of the various compounds mentioned above, thus increasing the amount of dissolved oxygen in the wastewater; combined with an increase in succharides such as glucose as described above, this promotes proliferation of flavobacteria and photosynthetic bacteria in the wastewater, thus improving the purification efficiency at purification facilities. Furthermore, the pineapple enzymes exhibit an unpleasant-odor-eliminating effect, decomposing malodorous components that emanate from wastewater such as sulfur compounds and lower fatty acids, and moreover converting ammonia gas and the like into harmless amino acids. Moreover, some inorganic chlorine compounds bind to the pineapple enzymes, and are thus made harmless. Furthermore, in purifier tanks and the like, sludge is decomposed and the amount of accumulation is reduced, and moreover the insides of drainage pipes are cleaned and hence the generation of unpleasant odors is prevented, and also scale in pipes is softened and removed, and thus it can be expected that the heat exchanger effectiveness in heat pumps and the like should improve. The various actions of the pineapple enzymes described above result in wastewater and drainage facilities and the like being cleaned, and in water pollution being ameliorated.

The above-mentioned pineapple enzymes are obtained in liquid or powder form by squeezing out pineapple juice, preferably under non-oxidizing conditions, and then concentrating or drying with the enzymes still in an active state. The pineapple enzymes contain a variety of enzymes that decompose macromolecular organic compounds, and since the pineapple enzymes can be readily obtained merely by squeezing out pineapple juice, manufacturing is cheaper than if the enzymes were synthesized artificially or extracted individually. Note that because the pineapple enzymes are used in a still active state, the pineapple enzymes would normally be used supported on powdered charcoal, clay or the like, or as a preparation in which the pineapple enzymes are impregnated into glucose, but in the present invention it is preferable to use the pineapple enzymes fixed to an inorganic powder, with this being done by adding pineapple juice to the inorganic powder and then fermenting, as described above.

The following is a list of principal components of the pineapple enzymes. The substances acted upon are given in parentheses.
Alcohol dehydrogenase (alcohols)
Lactate dehydrogenase (lactose)
Glucose-6-phosphate dehydrogenase (succharides)
Aldehyde dehydrogenase (aldehydes)
L-aspartate-β-semialdehyde NADP oxidoreductase (aldehydes)
Glutamate dehydrogenase (amino acids)
Aspartate-semialdehyde dehydrogenase (amino acids)
NADPH2-cytochrome-C-reductase (NADP)
Glutathione dehydrogenase (glutathione)
Trehalose-phosphate synthetase (succharides)
Polyphosphate kinase (ATP)
Ethanolamine phosphate cytidylyltransferase (CTP)
Trehalose-phosphatase (succharides)
Metalthio-phospho-glycerate phosphatase (glycerol)
Inulase (inulin)
β-mannosidase (succharides)
Uridine nucleosidase (amino acids)
Cytosine deaminase (cytosine)
Methylcysteine synthetase (amino acids)
Aspartate synthetase (ATP)
Succinate dehydrogenase (succinic acid)
Aconitate hydrogenase (citric acid)
Fumarate hydrogenase (malonic acid)
Malate dehydrogenase (malonic acid)
Citrate synthetase (acetyl-CoA)
Isocitrate dehydrogenase (citric acid)
LSNADP-Oxidactase (citric acid)
Monoamine-Oxidactase (amines)
Histaminase (amines)
Pyruvate decarboxylase (oxoacids)
ATPase (ATP)
Nucleotide pyrophosphatase (nucleic acids)
Endopolyphosphatase (ATP)
ATP phosphohydrolase (ATP)
Orotidine-5-phosphate decarboxylase (orotidine)
And other enzymes.

There are no particular limitations on the amount used of the above-mentioned pineapple enzymes in the detergent composition of the present invention. However, the larger the amount used, the larger the amount which will flow out into the wastewater and hence the stronger the cleaning action will be. It is thus preferable to fix at least about 0.1 wt % to the inorganic powder relative to the weight of the inorganic powder.

Moreover, there are no particular limitations on the type of the inorganic powder to which the pineapple enzymes are fixed. For example, a zeolite such as green zeolite or white zeolite, calcium carbonate, silica or the like may be used. Of these, if a porous material such as a zeolite is used, then due to the pores, the amount of pineapple enzymes that can be fixed to the inorganic powder will increase, and moreover the porous inorganic powder will adsorb pollutants, and hence it will be possible for the pineapple enzymes fixed to the porous inorganic powder to decompose the adsorbed pollutants or convert the adsorbed pollutants into harmless substances efficiently. Moreover, if an inorganic powder containing minerals, for example an alga fossil powder such as chlorella fossil powder or diatom fossil powder or a seashell powder such as oyster shell powder, is used, then the minerals contained in the powder act as a metabolite nutritional source for useful microorganisms, and hence useful microorganisms in wastewater and purifier tanks can be made abundant, and thus purification by microorganisms can be promoted. In particular, oyster shell powder contains in abundance over 100 types of mineral found in seawater, and is thus preferable as a mineral source for useful microorganisms. In the present invention, it is possible to use a plurality of powders having different special features in combination, for example a porous powder such as zeolite, a ceramic powder, and a mineral-containing powder such as oyster shell powder. That is, in the present invention, any of a variety of inorganic powders can be used either alone or with two or more types mixed together.

There are no particular limitations on the particle size of the inorganic powder, although the particle size is preferably no more than 50 μm, more preferably in a range of 20 to 30 μm. The smaller the particle size of the inorganic powder, the better the cleaning action on drainage pipes, purifier tanks and the like. However, if the particle size of the inorganic powder is too small, then there will be little abrasive effect. On the other hand, if the particle size of the inorganic powder is too big, then when cleaning metal tableware, sinks and the like, there will be a risk of the surfaces of these metal items being scratched and hence the luster being lost.

The soap used in the present invention is an alkali soap. Either a soda soap in which the cation is sodium or a potash soap in which the cation is potassium may be used. In the present invention, the soap may be in the form of either a powder or a liquid, and moreover a soap publicly known from hitherto may be used.

There are no particular limitations on the proportions of the inorganic powder and the soap in the detergent composition of the present invention. However, if the soap content is low, then the cleaning effects will be reduced, and hence it is preferable for the soap content in the detergent composition to be at least 1 wt %, preferably in a range of 1 to 5 wt %. Moreover, it is preferable for the inorganic powder content in the detergent composition to be at least 95 wt %. Furthermore, in addition to the soap and the inorganic powder to which pineapple enzymes have been fixed as described above, colloidal particles having adsorptive power and/or other auxiliaries may also be mixed into the detergent composition of the present invention.

The following method can be used to manufacture the detergent composition of the present invention. 1 wt % or more of pineapple juice relative to the weight of the inorganic powder is added to the inorganic powder, and then fermentation is carried out by leaving for at least 20 hours, preferably at least 36 hours, at a temperature of about 35 to 40° C., thus fixing pineapple enzymes to the inorganic powder. Soap and, if necessary, auxiliaries or the like are then mixed into the inorganic powder to which the pineapple enzymes have been fixed, thus obtaining the detergent composition.

BEST MODE FOR CARRYING OUT THE INVENTION

The present invention will now be described in detail through the following example. However, it should be noted that the present invention is not limited to this example in any way. (Formulation of detergent composition)

5 wt % of pineapple juice was added to an inorganic powder mixture (particle size not more than 50 μm) consisting of 79 wt % of zeolite powder, 10 wt % of alga fossil powder, 5 wt % of oyster shell powder and 1 wt % of ceramic powder, and reaction was carried out at 36° C. for one day and night, thus fixing pineapple enzymes to the inorganic powder. 1 wt % of soda soap was then mixed into the inorganic powder to which the pineapple enzymes had been fixed, thus obtaining a detergent composition.
(Cleaning Effects)

A stainless steel kitchen sink was cleaned using the above detergent composition, whereupon protein was completely removed, and tarnish on the stainless steel surface came off, with the luster of the stainless steel surface being restored almost beyond recognition. Moreover, when the detergent composition was used continuously, deposit attached to the inside of the drainage pipe connected to the sink came off completely, thus verifying the drainage pipe cleaning action of the detergent composition. Furthermore, it was found that the odor due to backflow from the purifier tank and the drainage pipes disappeared completely, and the functioning of the purifier tank improved.

INDUSTRIAL APPLICABILITY

According to the present invention, synthetic detergents that cause water pollution are not used, and moreover pineapple enzymes that have a water-cleaning action are contained in the detergent composition, and hence every time tableware, cooking appliances, sinks and the like are cleaned in a household, or tableware, food processing appliances, kitchen equipment and the like are cleaned at a food processing site, the pineapple enzymes are discharged with the wastewater from the cleaning through drainage pipes into a purifier tank, sewage water or the like. As a result, pollutants in the wastewater are made harmless by the pineapple enzymes, unpleasant odors are eliminated, and moreover the drainage pipes are cleaned, and the functioning of the purifier tank is improved, and hence water pollution is ameliorated.

What is claimed is:

1. A detergent composition, characterized by containing:

inorganic powder to which pineapple enzymes obtained from pineapple juice have been fixed; and a soap.

2. The detergent composition according to claim 1, wherein said detergent composition contains at least 95 wt % of said inorganic powder and at least 1 wt % of said soap.

3. The detergent composition according to claim 1, wherein said pineapple enzymes are fixed to said inorganic powder by adding pineapple juice to said inorganic powder and fermenting.

4. The detergent composition according to claim 1, wherein said inorganic powder is at least one selected from the group consisting of zeolite powder, calcium carbonate powder, silica powder, ceramic powder, alga fossil powder and seashell powder.

5. The detergent composition according to claim 1, wherein said inorganic powder is porous.

\* \* \* \* \*